United States Patent [19]

Kim et al.

[11] Patent Number: 4,851,762

[45] Date of Patent: Jul. 25, 1989

[54] NOVEL TECHNIQUE USING MAGNETIC FIELD DEPENDENT PHASE DETECTION FOR DETECTION OF SUPERCONDUCTIVITY

[75] Inventors: Boris F. Kim, Pasadena; Joseph Bohandy, Columbia; Kishin Moorjani, Silver Spring; Frank J. Adrain, Olney, all of Md.

[73] Assignee: The John Hopkins University, Baltimore, Md.

[21] Appl. No.: 238,682

[22] Filed: Aug. 31, 1988

[51] Int. Cl.$^4$ .................. G01N 27/14; G01R 27/04
[52] U.S. Cl. .................. 324/71.6; 324/58 C; 324/58 R; 324/233; 324/316; 505/843
[58] Field of Search .................. 324/316, 58 R, 58 C, 324/58 B, 58.5 C, 58.5 B, 233, 71.6, 62; 505/842, 843, 844, 847

[56] References Cited

U.S. PATENT DOCUMENTS 4,185,237  1/1980  Uehara et al. .................. 324/317
4,674,513  6/1987  Jasper, Jr. .................. 324/316

OTHER PUBLICATIONS

Khachaturyan et al., "Changes in Microwave Absorption of New High Tc Superconductors . . . ;" Mat. Res. Soc. Symp. Proc., vol. 99, pp. 383–386, Dec. 4, 1987.
Berlinger et al., "Two Multipurpose EPR Cavities . . . ," Rev. Sci. Instrum., vol. 48, No. 9, pp. 1161–1168, Sep. 1977.

Primary Examiner—Reinhard J. Eisenzopf
Assistant Examiner—Anthony L. Miele
Attorney, Agent, or Firm—Robert E. Archibald; Mary Louise Beall

[57] ABSTRACT

The invention relates to a method and apparatus to detect the superconductive state by measuring the change in the resistance of a sample. A dc magnetic field is imposed on the sample while the temperature is swept. The strength of the magnetic field is held below the critical value and is frequency modulated by the application of an ac field in such a way that total magnetic field is always positive. The resistance of the sample is measured incrementally as the temperature is swept and is phase detected at the modulation frequency. According to this embodiment, only magnetic field dependent changes demonstrating a precipitous drop in resistance identify a composition as superconductive.

39 Claims, 3 Drawing Sheets

NOVEL TECHNIQUE USING MAGNETIC FIELD DEPENDENT PHASE DETECTION FOR DETECTION OF SUPERCONDUCTIVITY

STATEMENT OF GOVERNMENTAL INTEREST

The Government has rights in this invention pursuant to Contract No. N00039-87-C-5301 awarded by the Department of the Navy.

BACKGROUND OF THE INVENTION

The invention relates to a method for detecting superconductivity. In particular, this invention uses resistance measurements at various temperatures and magnetic fields to determine the superconductive state.

Microwave absorption is one of several methods used to infer the presence of superconductivity in materials. This type of measurement has the advantage of being able to detect superconductivity in samples which are discontinuous. Microwave methods can also be very sensitive, permitting study of material samples which are very small. Most microwave methods involve the observation of the Q of a microwave resonator. More particularly, a waveguide cavity is used in a bridge in which reflected power from the cavity is recorded. Variations in the reflected power provide a measure of corresponding changes in the Q of the cavity. A sample located within the cavity affects the Q of the cavity by absorption of energy from the cavity fields. In applying this technique to the study of superconductors, the reflected power is measured as a function of the temperature of the sample which produces a sigmoid curve as shown in FIG. 1. This curve is similar to that produced in dc resistance measurements, indicating the transition to the superconducting state. However, many non-superconductive compositions, such as vanadium dioxide, also produce the same sigmoid curve.

Another technique useful in the determination of superconductivity uses a four-point probe to measure resistance. This technique is time consuming and requires a continuous sample, to which four leads are fixed.

U.S. Pat. No. 4,185,237 relates to a method of measuring the density of a material from a derivative absorption spectrum in a magnetic field sweep. Electron spin resonance (ESR) techniques are used wherein a sample is placed in a tube and set in an ESR cavity resonator. An ESR spectrum is measured by continuously sweeping the magnetic field while the microwave frequency to the cavity remains unchanged. Derivative peaks of a phase sensitive detector output are observed.

U.S. Pat. No. 3,805,119 discusses determining the characteristic of a superconductor by using the superconductor as the coil of a helical resonator which is mounted with its axis perpendicular to a variable d.c. magnetic field.

OBJECTS OF THE INVENTION

It is an object of the present invention to produce a method and apparatus for the rapid and accurate determination of superconductivity.

It is also an object of the present invention to provide a method and apparatus able to detect superconductivity in small and discontinuous samples.

It is also an object of the present invention to determine superconductivity by measuring the ac or dc resistance of a sample while varying one independent variable and maintaining the other below its critical value.

Another object of the present invention is a method and apparatus for the detection of the granularity of a superconductive sample.

SUMMARY OF THE INVENTION

The present invention relates to the detection of the superconductive state by measuring the electrical resistance of the sample. It is based on two principles:

1. At temperatures below the superconducting phase transition temperature ($T_c$), the resistance of the sample goes to zero, and
2. The superconductive phase transition temperature is magnetic field dependent.

The first principle is demonstrated graphically by FIG. 1. representing the amount of resistance in a sample in relation to temperature. The graph shows a precipitous drop in resistance.

According to the second principle, the application of a magnetic field at a strength below its critical value causes $T_c$ to drop to a lower value.

The invention combines both of these principles to make a method and apparatus able to accurately and rapidly determine the superconductive state. Both temperature and magnetic field are considered independent variables.

According to the invention, the resistance of the sample is measured while slowly changing one of the independent variables and also while modulating one of the independent variables at a defined frequency. The resistance is measured at the modulation frequency by phase detection. While one of the independent variables is being changed slowly, the other is maintained below its critical value. The critical value for the temperature is $T_c$ at zero magnetic field. The critical value for the magnetic field is defined as the maximum magnetic field the superconductive state can be subjected to at zero degrees Kelvin and still remain in the superconductive state.

In the preferred embodiment described below, a dc magnetic field is held constant below its critical value, the temperature is slowly changed or swept and the magnetic field is modulated by an ac magnetic field at a certain frequency. However, according to the invention, the temperature may be held constant below its critical value and modulated while the magnetic field is swept. In another configuration, the magnetic field is held constant below its critical value while the temperature is swept and modulated. It is also possible to hold the temperature constant and sweep and modulate the magnetic field.

If the magnetic field is modulated, the modulation must be such that the total field applied to the sample is always positive. In other words, the total field does not change direction. The temperature and magnetic field may be swept from high values to low values or vice versa.

Although all four variations of the method indicate the presence of the superconductive state, only two provide positive identification. These are the embodiment in which the magnetic field is modulated while the temperature is swept and the embodiment in which the temperature is modulated and the magnetic field is swept. In the second and fourth embodiments described above, the final result plotted on an x-y graph is the derivative of the resistance with respect to the magnetic field. The other two embodiments result in a graph of the derivative of the resistance with respect to temperature.

The following calculations demonstrate that, in the region of phase transition, results obtained using field modulation are equivalent to those using temperature modulation. If a constant field (H<Hc) is imposed on the sample and the temperature is scanned, but the field is modulated, the signal recorded is (apart from a constant factor):

$$S = \left(\frac{dP}{dH}\right)_T \delta H.$$

It can readily be seen from FIG. 3 that $$\Delta P = P(H + \delta H, T) - P(H, T) = \left(\frac{dP}{dH}\right)_T \delta H =$$

$$P(H, T + \delta T) - P(H, T) = \left(\frac{dP}{dT}\right)_H \delta T$$

therefore, $$\left(\frac{dP}{dH}\right)_T \delta H = \left(\frac{dP}{dT}\right)_H \delta T$$

wherein P=detected power.

In the two embodiments wherein the temperature is swept, measuring the resistance of the sample requires that the temperature of the sample be recorded at each temperature change, producing first signals. Second signals are produced by measuring the resistance of the sample at each temperature change. The second signal is compared to the modulation frequency by phase detection and produces third signals. The first and third signals are used to plot a series of coordinate points on a graph wherein one axis represents the temperature or first signals and the other axis represents the derivative of the phase detected resistance with respect to the temperature. The precipitous drop in resistance is expressed by a peak formed on the graph. $T_c$ is identified by the location of the peak on the temperature axis of the graph.

For the embodiments wherein the magnetic field is swept, resistance measurement is similar to that described above. The strength of the magnetic field is recorded at each change, producing first signals. Second signals are produced by measuring the resistance of the sample at each field change. The second signal is compared to the modulation frequency by phase detection and produces third signals. The first and third signals are used to plot a series coordinate points on a graph wherein one axis represents the field or first signals and the other axis represents the derivative of the phase detected resistance with respect to the field or third signals. As above, the precipitous drop in resistance is expressed by a peak formed on the graph.

The resistance can be measured in any one of several resistance measuring devices including a resonant cavity, a resonant circuit and a four-point probe.

DESCRIPTION OF A PREFERRED EMBODIMENT

Figure 4:
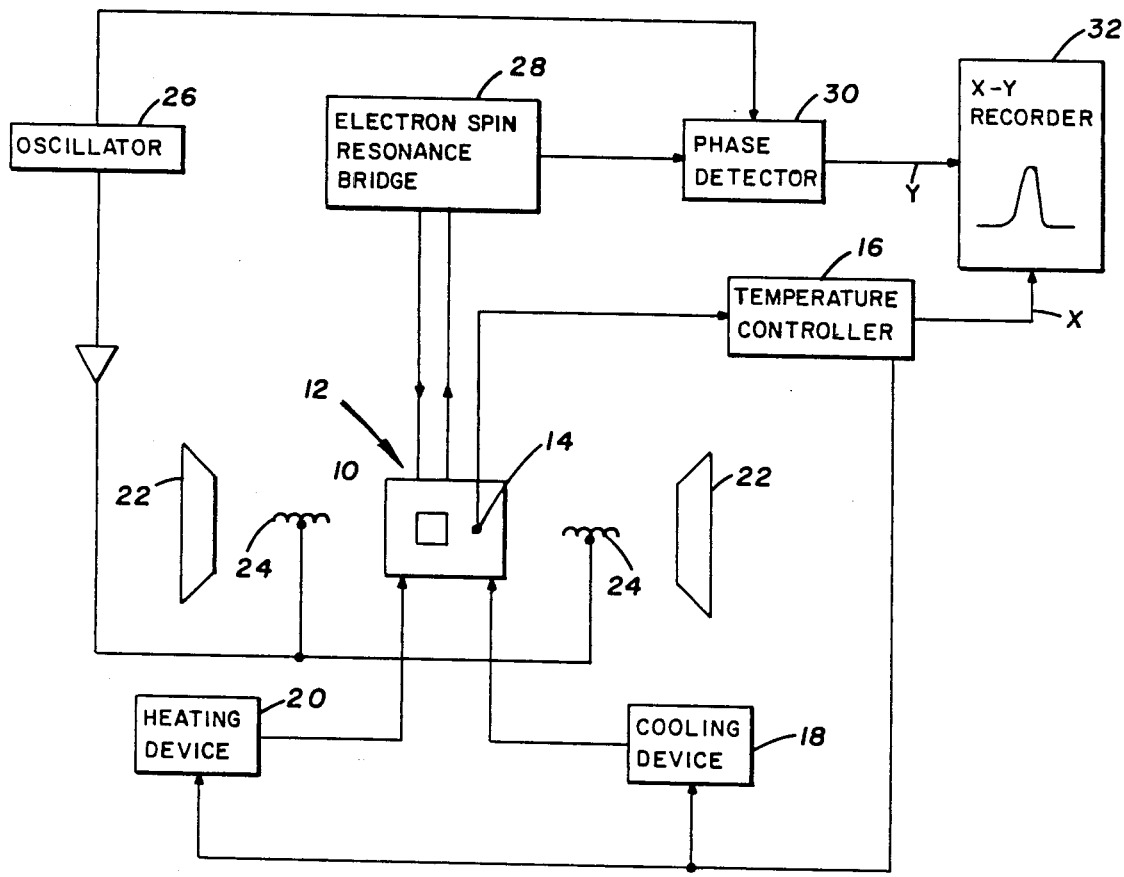
FIG. 4 is a block diagram of the apparatus of the invention.

The preferred embodiment uses a microwave resonant cavity to measure the microwave resistance of the sample. In FIG. 4 wherein a sample 10 is placed in a resonant microwave cavity 12 provided with a temperature sensor 14. The temperature sensor is connected to a temperature controller 16 controlling the temperature of sample 10 with cooling device 18 and heating device 20.

A constant dc magnetic field is applied to cavity 12 and thus to sample 10 by magnet 22. This field is modulated by the application of an ac frequency supplied by oscillator 26 through field modulation coils 24. At all times the total magnetic field is positive (does not change direction) and below the critical value.

Microwave energy is imposed on sample 10 in cavity 12 via a microwave bridge 28 provided with a microwave detector. The microwave frequency is locked to the resonant frequency of the cavity by standard automatic frequency control methods. Oscillator 26 and the microwave detector in microwave bridge 28 are both connected to phase detector 30 which compares the microwave signal to the signal from oscillator 26. As the temperature is changed or swept, changes in microwave absorption, detected by the microwave detector are phase detected at the modulation frequency by phase detector 30. Computer signals "y" from phase detector 30 and related computer signals "x" from temperature controller 16 form coordinate points on an x-y recorder 32.

Figure 1:
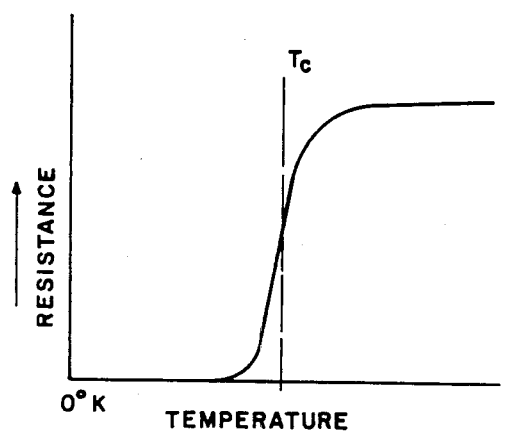
FIG. 1 is a typical curve produced by measuring the resistance of a specimen, as a function of specimen temperature.

The microwave resistance of sample 10 affects the Q (quality factor) of cavity 12. The microwave signal detected by microwave bridge 28 is microwave power reflected from cavity 12. This reflected power depends upon the coupling match between the cavity and the transmission medium (waveguide or cable), not shown, feeding the cavity. The match is affected by the cavity Q. Thus, changes in the microwave resistance of sample 10 in cavity 12 result in corresponding changes in the coupling match and therefore in the reflected power. The change in reflected power which results from a precipitous drop in microwave resistance of the sample 10 produces a change in reflected power similar to that shown in FIG. 1.

Figure 2:
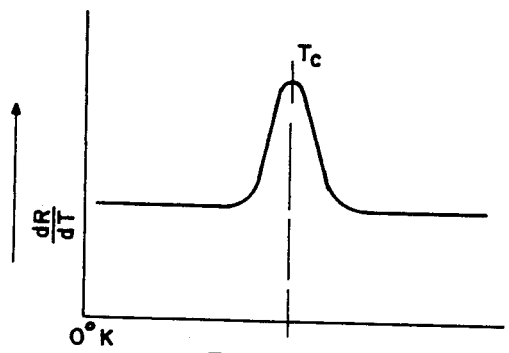
FIG. 2 is a curve derived from the FIG. 1 curve.
Figure 3:
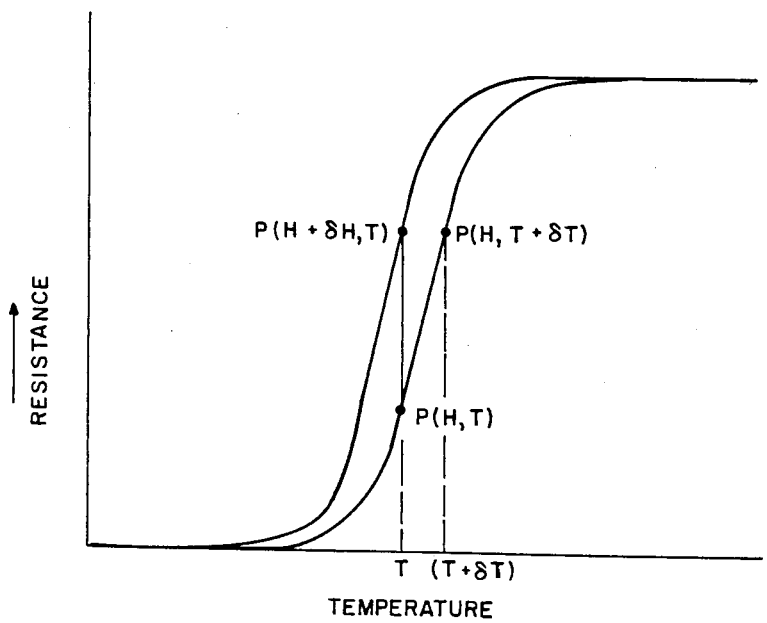
FIG. 3 is a graph representing the magnetic field dependence of resistance vs temperature for a superconductor.

Because the microwave signal is modulated at a certain frequency and phase detected at that same frequency, its derivative, shown as the bell shaped curve or peak in FIG. 2, is the response actually recorded on x-y recorder 32. Thus, the modulation of the reflected microwave signal is the actual quantity measured. The presentation of the characteristic peak on the x-y recorder indicates that the specimen exhibits a precipitous loss of resistance at $T_c$ and that $T_c$ is magnetic field dependent. The location of the peak on the x-y graph also provides $T_c$ since the "x" computer signal represents temperature.

Figure 5:
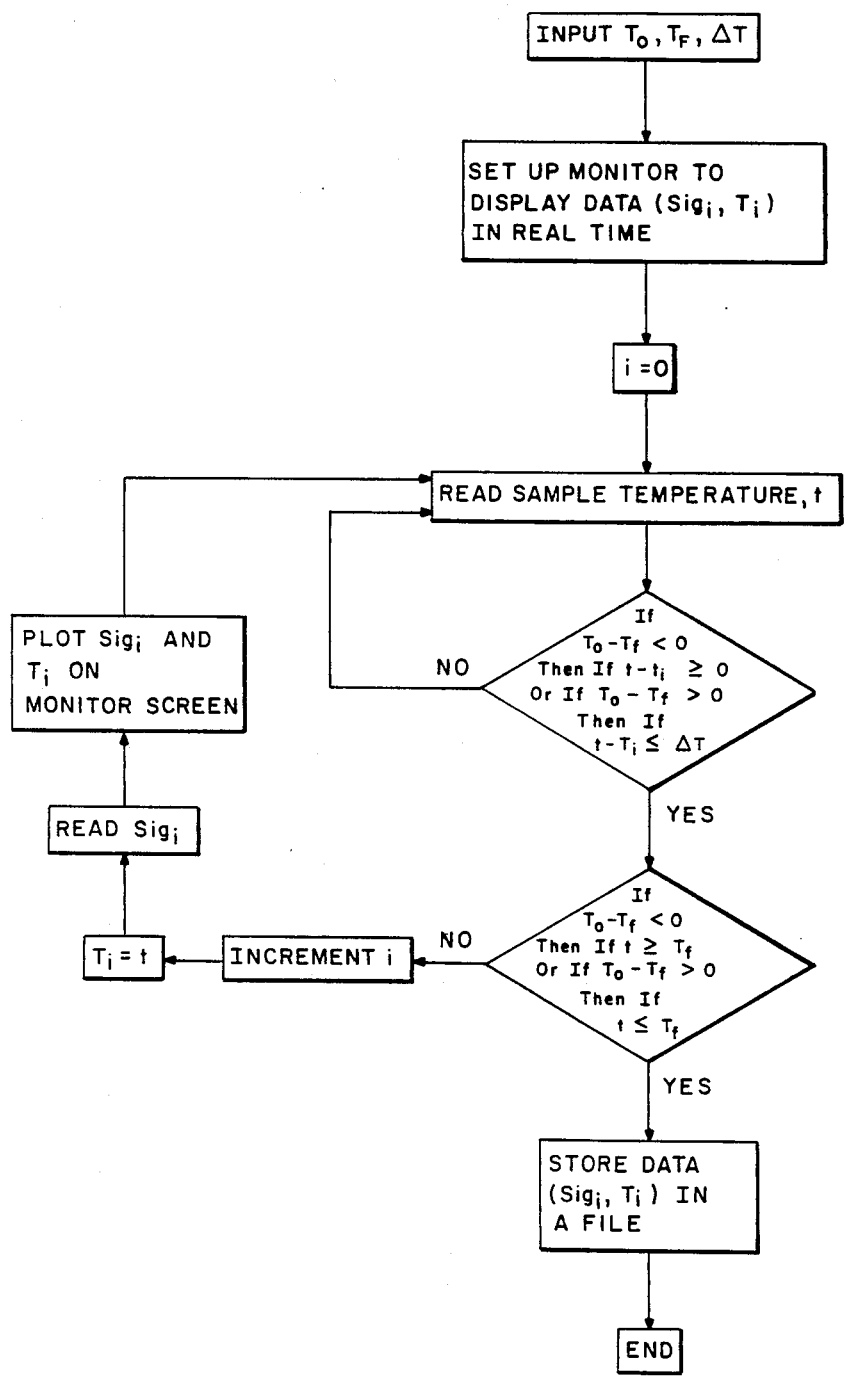
FIG. 5 is a flow chart of the software of the present invention.

Computer means, not shown, are required to operate the process and apparatus of the invention. FIG. 5 is a flow diagram of the software wherein:

$T_o$ = the starting or initial sample temperature to be recorded.

$T_f$ = the final sample temperature to be recorded.

$\Delta T$ = the temperature sampling increment.

Sig = the phase detected microwave signal.

The phase detected microwave signal (signals "y" from phase detector 30) and the related temperature (signals "x" from temperature controller 16) are recorded only at equal preselected temperature increments $\Delta T$ in a linear temperature progression. Temperature is obtained by reading a thermocouple voltage which is converted to temperature by software means (not shown in the flow diagram).

The method and apparatus of this embodiment of the invention detect only magnetic field dependent changes in microwave resistivity and record the derivative of the microwave signal as a function of temperature. Since the metal/insulator phase transition is not magnetic field dependent, only superconducting phase transitions are recorded.

This method and apparatus can also be used to identify multiple superconducting phases characterized by different $T_c$'s because multiple transition peaks can easily be recorded. Only a very small sample is required and discontinuous or granular samples may be used. Also, the magnetic field dependence of the superconducting phase transition temperature may be measured as well as the temperature dependence of the superconducting phase transition field.

The invention may be used to measure the state of granularity of a sample. At temperatures below $T_c$, the presence of Josephson junctions with associated tunneling currents causes noise in the microwave response, the amount of which is an indication of the state of granularity. Josephson junctions can be described as regions of superconductivity separated by regions of non-superconductivity through which superconducting current can tunnel. The amount of noise decreases with decreasing sample granularity.

The dc magnetic field applied to the sample has a strength in the range 30 to 5,000 gauss. The ac frequency modulation is in the range of 1 Hertz to 100 Kilo Hertz and is typically on the order of 10 Kilo Hertz. The temperature range swept depends on the nature of the sample but at least includes several degrees Kelvin above and below the sample's $T_c$. $\Delta T$ is on the order of 0.2° Kelvin, for example. If a microwave cavity is used, the microwave power imposed is approximately 1 to 200 milliwatts. The amplitude of the magnetic field modulation is in the range of 50 milligauss to 10 gauss.

The invention described is not intended to be limited to the embodiments disclosed but includes modifications made within the true spirit and scope of the invention.

What is claimed is:

1. A method for detecting superconductivity and the superconductive phase transition comprising:
    providing a resistance measuring device;
    placing a sample within a device;
    imposing a magnetic field on the sample;
    sequentially changing one of the temperature of the sample and the magnetic field while maintaining the other below its critical value and while modulating one of said temperature and magnetic field at a known frequency in such a fashion that the total magnetic field is always positive; and
    measuring the resistance of the sample by phase detection at said modulating frequency;
    wherein only changes in resistance occuring at the modulating frequency and demonstrating a precipitous drop in resistance indicate the presence of superconductivity.

2. A method according to claim 1, wherein the temperature is sequentially changed while the magnetic field is modulated.

3. A method according to claim 2, wherein the resistance measuring device is a resonant cavity and microwave power is imposed on the sample.

4. A method according to claim 3, wherein the measuring step comprises:
    recording the temperature at each change and producing first signals;
    measuring the amount of microwave power reflected from the cavity at each temperature change and producing second signals;
    comparing the second signals to the modulation frequency by phase detection and producing third signals; and
    plotting a series of coordinate points wherein one axis represents said first signals and the other axis represents said third signals.

5. A method according to claim 4, wherein the temperature is recorded and the reflected microwave power is measured only at equal preselected temperature increments in a linear temperature progression.

6. A method according to claim 5, wherein the imposed magnetic field is in the range of 30-5000 gauss, the modulation frequency is in the range of 1 Hertz-100 Kilo Hertz, the microwave power is in the range of 1-200 milliwatts and temperature increment is on the order of 0.2° C.

7. A method according to claim 4, wherein said first signal is the temperature and said third signal is a derivative of said phase detected reflected microwave power with respect to the temperature.

8. A method according to claim 7, wherein the precipitous drop resistance is expressed by a peak formed by the series of 9. A method according to claim 1, wherein the temperature is sequentially changed while the temperature is modulated.

10. A method according to claims 2 or 9, wherein the temperature is sequentially changed and wherein the measuring step comprises:
    recording the temperature at each change and producing first signals;
    measuring the resistance of the sample at each temperature change and producing second signals;
    comparing the second signals to the modulation frequency by phase detection and producing third signals; and
    plotting a series of coordinate points wherein one axis represents said first signals and the other axis represents said third signals.

11. A method according to claim 10, wherein the temperature is recorded and the resistance is measured only at equal preselected temperature increments in a linear temperature progression.

12. A method according to claim 10, wherein said first signal is the temperature and said third signal is a derivative of said phase detected resistance with respect to the temperature.

13. A method according to claim 10, wherein the precipitous drop in resistance is expressed by a peak formed by the series of coordinate points and wherein $T_c$ is identified by the location of the peak in reference to said one axis representing said first signals 14. A method according to claim 1, wherein the magnetic field is sequentially changed while the magnetic field is modulated.

15. A method according to claim 1, wherein the magnetic field is sequentially changed while the temperature is modulated.

16. A method according to claims 14 or 15, wherein the magnetic field is sequentially changed and wherein the measuring step comprises:
    recording the strength of the magnetic field at each change and producing first signals;
    measuring the resistance of the sample at each magnetic field change and producing second signals;
    comparing the second signals to the modulation frequency by phase detection and producing third signals; and
    plotting a series of coordinate points where one axis represents said first signals and the other axis represents said third signals.

17. A method according to claim 16, wherein the strength of the magnetic field is recorded and the resistance is measured only at equal preselected magnetic field increments in a linear progression.

18. A method according to claim 16, wherein said first signal is the strength of the magnetic field and said third signal is a derivative of said phase detected resistance with respect to the magnetic field.

19. A method according to claim 16, wherein the precipitous drop in resistance is expressed by a peak formed by the series of coordinate points.

20. A method according to claim 1, wherein the resistance measuring device is one of a resonant cavity, a resonant circuit, a two point probe and a four point probe.

21. An apparatus for detecting superconductivity and the superconductive phase transition comprising:
    a resistance measuring device;
    means imposing a magnetic field on a sample within the device;
    means sequentially changing one of the temperature of the sample and the magnetic field while maintaining the other below its critical value;
    means modulating one of said temperature and magnetic field at a known frequency while one of said temperature and magnetic field is sequentially changed and in such a way that the total magnetic field is always positive; and
    means measuring the resistance of the sample by phase detection at said modulating frequency;
    wherein only changes in the resistance occurring at the modulating frequency and demonstrating a precipitous drop in resistance indicate the presence of superconductivity.

22. An apparatus according to claim 20, wherein the temperature is sequentially changed while the magnetic field is modulated.

23. An apparatus according to claim 22, wherein the resistance measuring device is one of a resonant cavity, a resonant circuit, a two-point probe and a four-point probe.

24. An apparatus according to claim 23, wherein the resistance measuring device is a resonant cavity, wherein the apparatus includes means to impose microwave power on the sample.

25. An apparatus according to claim 24, wherein the means measuring comprises:
    means measuring the temperature of the sample;
    means to record the temperature at each change and produce first signals;
    a microwave detector measuring microwave power reflected from the cavity at each temperature change and producing second signals;
    a phase detector comparing the second signals to the modulation frequency by phase detection and producing third signals;
    an x-y recorder; and
    means combining said first and third signals to plot a series of coordinate points on the x-y recorder wherein one axis represents said first signals and the other axis represents said third signals.

26. An apparatus according to claim 25, wherein the means measuring the temperature is recorded and the reflected microwave power is measured only at equal preselected temperature increments in a linear temperature progression.

27. An apparatus according to claim 25, wherein said first signal is a derivative of the temperature and said third signal is a derivative of said phase detected reflected microwave power.

28. An apparatus according to claim 27, wherein the precipitous drop in resistance is expressed by a peak formed by the series of coordinate points and wherein $T_c$ is identified by the location of the peak in reference to said one axis representing said first signals.

29. An apparatus according to claim 21, wherein the temperature is sequentially changed while the temperature is modulated.

30. An apparatus according to claims 22 or 29, wherein the temperature is sequentially changed and wherein the means measuring comprises:
    means measuring the temperature of the sample;
    means to record the temperature at each change and produce first signals;
    a resistance measuring device measuring the resistance of the sample at each temperature change and producing second signals;
    a phase detector comparing the second signals to the modulation frequency by phase detection and producing third signals;
    an x-y recorder; and
    means combining said first and third signals to plot a series of coordinate points on the x-y recorder wherein one axis represents said first signals and the other axis represents said third signals.

31. An apparatus according to claim 30, wherein the means measuring the temperature is recorded and the resistance is measured only at equal preselected temperature increments in a linear temperature progression.

32. An apparatus according to claim 30, wherein the said first signal is the temperature and said third signal is a derivative of said phase detected resistance with respect to the temperature.

33. An apparatus according to claim 30, wherein the precipitous drop in resistance is expressed by a peak formed by the series of coordinate points and wherein $T_c$ is identified by the location of the peak in reference to said one axis representing said first signals.

34. An apparatus according to claim 21, wherein the magnetic field is sequentially changed while the magnetic field is modulated.

35. An apparatus according to claim 21, wherein the magnetic field is sequentially changed while the temperature is modulated.

36. An apparatus according to claims 34 or 35, wherein the magnetic field is sequentially changed and the means measuring comprises:
   means measuring the strength or the magnetic field of the sample;
   means to record strength of the magnetic field at each change and produce first signals;
   a resistance measuring device measuring resistance of the sample at each change of the magnetic field and producing second signals;
   a phase detector comparing the second signals to the modulation frequency by phase detection and producing third signals;
   an x-y recorder; and
   means combining said first and third signals to plot a series of coordinate points on the x-y recorder wherein one axis represents said first signals and the other axis represents said third signals.

37. An apparatus according to claim 36, wherein the strength of the magnetic field is recorded and the resistance is measured only at equal preselected magnetic field increments in a linear progression.

38. An apparatus according to claim 36, wherein said first signal is the strength of the magnetic field and said third signal is a derivative of said phase detected resistance with respect to the magnetic field.

39. An apparatus according to claim 36, wherein the precipitous drop in resistance is expressed by a peak formed by the series of coordinate points.

* * * * *

UNITED STATES PATENT AND TRADEMARK OFFICE
CERTIFICATE OF CORRECTION

PATENT NO. : 4,851,762
DATED : July 25, 1989
INVENTOR(S) : Kim et al.

It is certified that error appears in the above—identified patent and that said Letters Patent is hereby corrected as shown below:

In the designation of Inventors on the title page,

"Frank J. Adrain" should read -- Frank J. Adrian --

In the designation of Assignee on the title page,

"The John Hopkins University" should read -- The Johns Hopkins University --

<u>In the claims:</u>

Column 6, line 44, after "series of" insert -- coordinate points and wherein $T_c$ is identified by the location of the peak in reference to said one axis representing said first signals. --

Signed and Sealed this

Fifth Day of June, 1990

*Attest:*

HARRY F. MANBECK, JR.

*Attesting Officer*     *Commissioner of Patents and Trademarks*